US00PP10186P

United States Patent [19]

Osiecki

[11] Patent Number: Plant 10,186

[45] Date of Patent: Jan. 6, 1998

[54] ANTHURIUM PLANT 'A1'

[75] Inventor: Marian W. Osiecki, Marianna, Fla.

[73] Assignee: Oglesby Plant Laboratories, Inc., Altha, Fla.

[21] Appl. No.: 706,908

[22] Filed: Sep. 3, 1996

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 8,129 2/1993 Georgusis ..... Plt./88.1

P.P. 8,131 2/1993 Georgusis ..... Plt./88.1

*Primary Examiner*—James R. Feyrer
*Assistant Examiner*—Kent L. Bell
*Attorney, Agent, or Firm*—Rothwell, Figg, Ernst & Kurz

[57] ABSTRACT

A new variety of Anthurium is provided. It is a medium size, relatively open plant, suitable for production in 15 cm to 25 cm pots from a single tissue culture produced microcutting with vigorous growth; early and abundant branching; early and abundant flowering; dark green, glossy, thick, leathery leaves, sharply contrasting with medium size, white spathes (with relatively dark spadixes) held above and at the level of foliage on strong peduncles.

2 Drawing Sheets

SUMMARY OF THE INVENTION

This invention relates to a new and distinct Anthurium cultivar characterized by the following combination of repeatedly observed traits:

1. Medium size,
2. relatively open growth habit,
3. vigorous growth,
4. early and abundant branching,
5. dark green, glossy, thick, leathery leaves,
6. early, abundant and year-round flowering,
7. inflorescence of good quality from the onset of flowering,
8. medium size spathes held on strong peduncles above and at the level of foliage,
9. sharp contrast between white spathes and dark foliage,
10. good contrast between spathe and spadix;

and primarily selected for those characteristics being so selected from the progeny of the cross stated below being grown near Altha, Fla. in a cultivated area.

Origin and Asexual Reproduction

Asexual reproduction of this cultivar by tissue culture was directed by me, such reproduction establishing that the plant does in fact maintain the characteristics described, in successive generations.

The plant was initially selected where grown in a planned breeding program in or near Altha, Fla. and has since been reproduced by plant tissue culture in the vicinity of Altha, Fla. with the characteristics stated. The female parent was a selection of *Anthurium antioquense* designated II and the male parent was a selection of white *Anthurium andreanum* designated AW 891. The cross was made in 1991 and the seedling was selected in 1992.

The new cultivar has been identified as Anthurium 'A1'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'A1' was approximately 14 months from planting a single tissue cultured microcutting and was grown in a 20 cm pot.

In the photographs:

DETAILED DESCRIPTION OF THE NEW CULTIVAR

Figure 1:
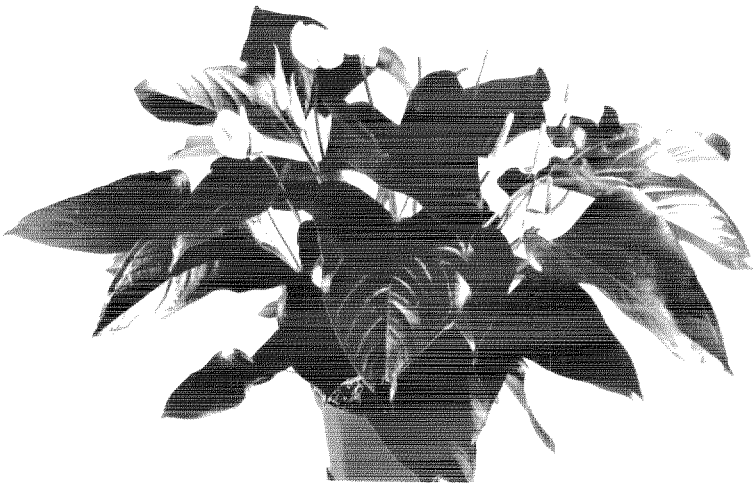
FIG. 1 depicts the whole plant.
Figure 2:
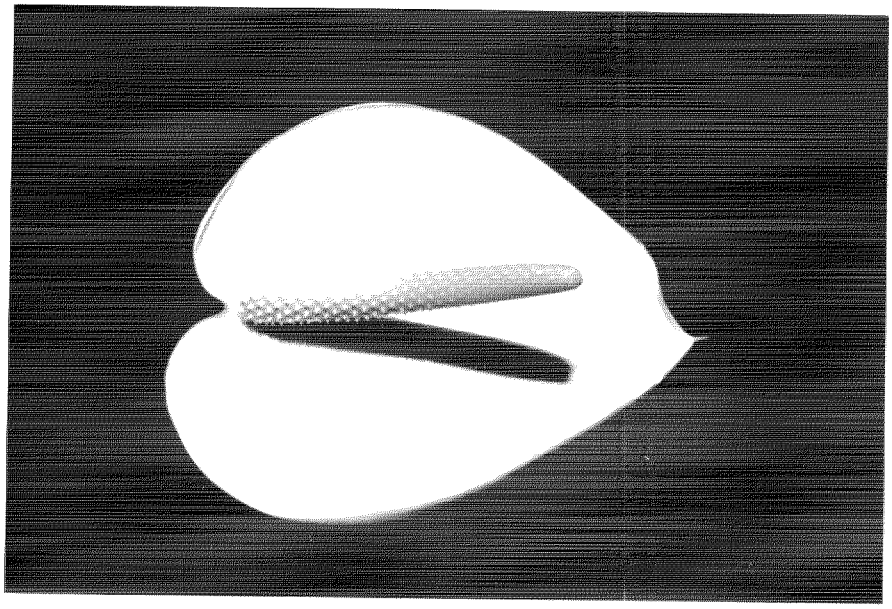
FIG. 2 illustrates the mature inflorescence.
Figure 3:
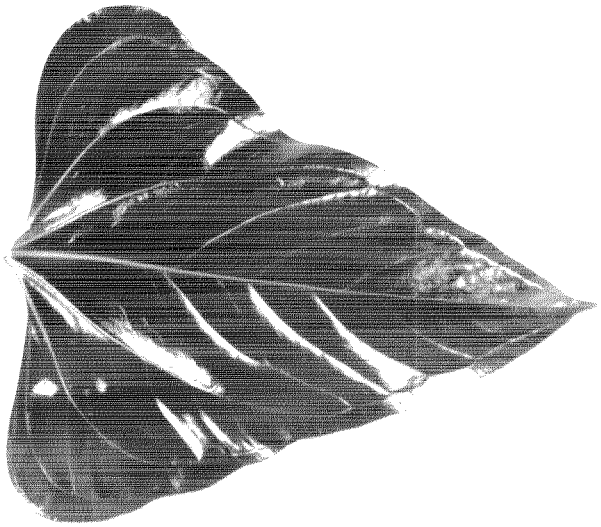
FIG. 3 illustrates a top of a mature leaf.
Figure 4:
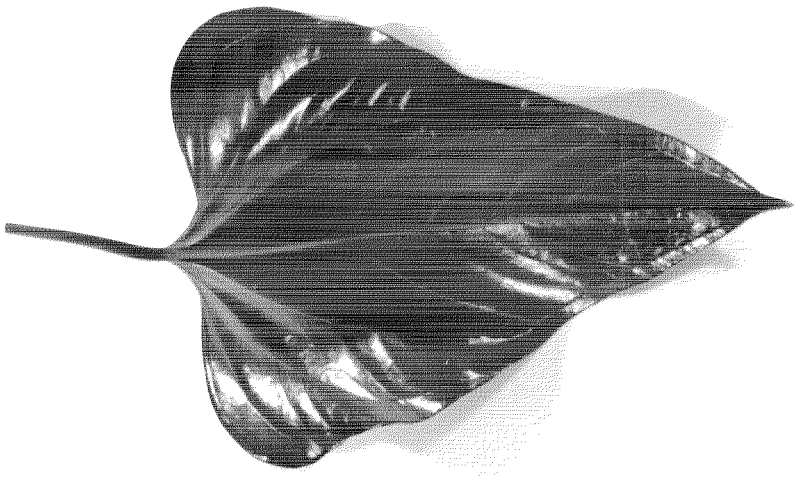
FIG. 4 illustrates the bottom of a mature leaf.

The following observations and measurements describe plants grown near Altha, Fla. under greenhouse conditions. These observations and measurements were recorded in September, 1995 from mature plants (about 18 months from planting tissue cultured microcuttings) grown in 15 cm pots. Fully developed organs on the main stem were used for measurements. Color values were determined on Sep. 21, 1995 under natural, indirect light of approximately 450 foot-candles. Color references are made to The R.H.S. Color Chart, except where general color terms of ordinary significance are used.

'A1' has not been observed under all possible environmental conditions. The phenotype may vary with variations in environment and horticultural practices, such as temperature, light intensity, day length, fertilization and propagation procedure, without any change in genotype.

Parentage:

*Female parent.*—*Anthurium antioquense* "II".

*Male parent.*—*Anthurium andreanum* "AW 891".

Propagation: Plant tissue culture started near Altha, Fla.

Plant descriptions:

*Growth habit.*—Medium size, with short stems well branched, relatively open.

*Height.*—Foliage 36–43 cm; with spathes 43–50 cm.

*Width.*—65–80 cm.

Petiole:

*Size.*—26–31 cm long, 5.0–5.3 mm in diameter at the mid length; cross section round at the mid length.

*Geniculum.*—3.2–3.5 cm long, 6.0–6.5 mm in diameter, not very prominent.

*Petiole wings.*—Not conspicuous, 2.8–3.4 cm long.

*Color.*—Geniculum: Front—146A at the base with some lighter color (146B) close to the juncture with leaf blade. Back—Darker than 144A; the base slightly darker than the juncture with leaf blade. Below geniculum: Front—Most similar to 146A with some resemblance to 147B and 137C; proximally gradually darker with a strong resemblance to 147A at the base. Back—Similar to 146A, B and 147B, proximally gradually darker with some resemblance to 147A at the base. Petiole wings: Similar to 147A with some resemblance to 146A.

Leaf blade:

*Position.*—Midrib of most leaves approximates horizontal position or points slightly down from horizontal; large newly unfolded leaves reflexed.

*Shape.*—Between ovate and deltoid, slightly asymmetric; tip between acuminate and cuspidate, usually slightly curved; base truncate. The basal half of the blade on each side of the midrib curves upward. Leaf margin usually slightly wavy, especially in the basal half. Leaves produced at early stage of development are flat, have more obtuse bases and a non wavy margin.

*Size.*—25.5–27.5 cm long; 19.2–22.0 cm wide; length to width ratio 1.2–1.3:1.

*Texture.*—Thick, leathery, smooth, glossy; young leaves highly polished.

*Veins.*—Very prominent near the base, inconspicuous near the tip. Midrib protrudes from the upper leaf blade surface for approximately ⅔ of its length from the base and is somewhat sunken closer to the tip. Well defined primary veins (usually 6–8) radiate from the juncture of the leaf blade and the petiole. The first primary vein on each side of the midrib protrudes for no more than ½ of the blade's length and the adjacent primary veins protrude for a smaller portion of the blade's length. The remaining primary veins are entirely sunken. Midrib and all primary veins protrude from the lower surface of the leaf blade.

*Color.*—Newly unfolded leaf: Upper surface—similar to 147A; protruding portions of the veins—146B-C. Lower surface—147B; veins lighter than 144A with some resemblance to 144B and 145A. Mature Leaf: Upper surface—Much darker than 147A; protruding portions of the veins: 146A-B. Lower surface—Lighter than 147A, darker than 147B; veins—most of the midrib and primary veins close to the base most similar to 144A with some resemblance to 146B; the remaining part of the veins similar in color to the surrounding tissue.

Scale leaf covering lateral vegetative bud (opposite to the mature inflorescence):

*Length.*—14.0–15.3 cm.

*Color.13* Base (up to 1–1.5 cm high) has various colors including: 146D, a color lighter than 146D, 146C and 144 B-D; the lightest colors appear at the bottom. Above the base, central zone is similar to 146A and the sides are similar to 144A with some resemblance to 146A-B.

Scale leaf between peduncle of a young inflorescence and the stem:

*Length.*—3.9–4.8 cm.

*Color.*—Two protruding ribs—144A; areas between and outside the ribs—much lighter and a little translucent consist of the shades of and between 144B-D and 145B-D.

Inflorescence:

*Arrangement.*—Most spathes carried above or near the level of foliage on strong, usually straight peduncles. Sometimes peduncle slightly curves approximately 1 cm below the juncture with the spathe. Spadix large in relation to spathe (ratio spathe length to spadix length 1.2–1.5:1) and situated low on the spathe.

Development: In a newly opened inflorescence usually spadix bends backwards or is almost vertical and the spathe is almost parallel to the spadix. Within a few days spathe becomes reflexed and the spadix becomes more vertical or remains unchanged. Later spathe gradually rises and at maturity resumes a horizontal or higher position forming an angle between 45 to 90 degrees with the spadix; tip curves backwards. Spadix remains vertical or slightly bent backwards.

Peduncle:

*Size.*—36.5–39.2 cm long; 3.7–4.9 mm in diameter at the mid length; cross section approximately round; 4–5 mm from front spathe—attaching position to spadix base; stipe approximately 1 mm long.

*Color immediately below mature spathe.*—Front: Similar to, but darker than 144A with some resemblance to 146A, B. Back: 144A. Front and back of peduncle become a little darker towards the base.

Spathe:

*Shape.*—Ovate, at maturity almost flat or slightly curving backwards, with small ridges radiating from the juncture with peduncle; tip—between cuspidate, acuminate and aristate, slightly curved with the edges rolling frontwards; base—cordate sometimes slightly asymmetric; two rounded lobes extend 0.9–1.3 cm (9.5–13.0% of the spathe's length) in front of peduncle.

*Size (flattened).*—8.0–10.6 cm long, 6.4–7.7 cm wide; length to width ratio 1.2–1.4:1.

*Texture.*—Smooth, glossy.

*Color.*—Closed bud: Similar to 155A, B, D. Newly open spathe: Front—A little darker than 155D (white) with variable amount and intensity of pink coloration between the veins; most spathes are almost entirely white or have some patches of 36D; some spathes have some darker color—almost 51D or 54D, especially close to the base; pink coloration is always most intense in lobe portions in front of peduncle and gradually fades towards the tip. Back—A little darker than 155D. Mature spathe: Front—Similar to 155D. Back—Similar to 155B and 155D.

*Veins.*—Inconspicuous; in the basal half on the slightly elevated ridges.

Spadix:

*Shape.*—Columnar, slightly tapering in the distal half.

*Size.*—5.4–6.9 cm long, 7.2–8.4 mm in diameter.

*Color.*—Changes dramatically between time of spathe opening and pollen expulsion. Young—no pistils visible to the naked eye: Basal approximately ¼ of spadix, where pistils start protruding—the hue is similar to 54C and intensity similar to 66D; merges with 35C, which dominates the next ⅓–½ of the spadix and merges with 11B of the tip; in the back 11B extends further down than in the front. The basal red zone gradually expands and becomes darker at the bottom, especially in front, as the middle orange-red zone shrinks. Mature—pistils visible on approximately ¾ of the spadix length: Basal zone with visible stigmas shows a slight gradation of color from the lightest at the bottom (similar to 55C, D and 54D) to the darkest at the top (between 54C and 55B); the upper zone, with no visible stigmas is similar to, but usually lighter than 51B and darker than 51C or 50C; tip is 35C, sometimes with some 11B; when pistils are visible on the entire length of spadix, the base of the spadix is between 55D and 63D and the distal portion is similar to 63C, 62B and 55B except for the tip, which is 51B.

Botanical flower:

*Perianth.*—Easily visible between pistils, determines the color of the spadix, segments united.

*pistil.*—Not visible immediately after spathe opening, at maturity distinctly lighter than perianth; stigmas well visible.

*Stamens.*—Not visible before pollen release.

Flowering: Flowers naturally in 15 cm pots, about 9–11 months from planting tissue cultured microcuttings. Continuous year-round flowering. One to four spathes constantly visible above or among leaves.

Spathe longevity: Spathe remains white for up to 7.5 weeks following emergence of bud above or among foliage and then gradually changes to a green color.

Roots: Roots developed above soil line are thick, fleshy and non-branching; they usually develop inside of and stay tightly wrapped by the scale leaves until their senescence. Roots developed below soil line are fleshy, branched with fine lateral roots, cream in color with yellow root caps.

Disease and insect resistance: No unusual susceptibility to diseases or insects noted to date.

Comparison with the known cultivars

The new cultivar can be compared to the known cultivar 'Georgusis White Number 1', U.S. Plant Pat. No. 8,129 a/k/a Lady Anne. The comparisons were made on plants grown under similar conditions in a greenhouse near Altha, Fla.

'A1' is distinguished from 'Georgusis White Number 1' by its earlier branching and earlier and more abundant flowering. 'A1' is further distinguished from 'Georgusis White Number 1' by its larger spathes with less pink coloration, which is retained for a shorter time after opening; longer (more aristate) spathe tip; larger and darker spadixes better contrasting with the spathe; thicker and stronger peduncles; darker, glossier, substantially wider and usually shorter leaf blades with more erect lobes; less susceptibility to nutrient disorders and low temperature damage.

I claim:

1. A new and distinct cultivar of Anthurium plant named 'A1', substantially as described and illustrated herein, characterized particularly as to novelty by its medium size; vigorous growth; early and abundant branching; early, abundant and year-round flowering; dark green, glossy, thick leaves; inflorescences of good quality from the onset of flowering; medium size white spathes with limited pink coloration held on strong peduncles above and at the level of foliage.

* * * * *